United States Patent [19]

Masri et al.

[11] 4,089,746

[45] May 16, 1978

[54] METHOD FOR INSOLUBILIZING ENZYMES ON CHITOSAN

[75] Inventors: Merle S. Masri, Emeryville; Virginia G. Randall; William L. Stanley, both of El Cerrito, all of Calif.

[73] Assignee: The United States of America as represented by the Secretary of Agriculture, Washington, D.C.

[21] Appl. No.: 706,980

[22] Filed: Jul. 19, 1976

[51] Int. Cl.² ............................................. C07G 7/02
[52] U.S. Cl. .................................... 195/63; 195/68; 195/DIG. 11
[58] Field of Search .................... 195/63, 68, DIG. 11

[56] References Cited

U.S. PATENT DOCUMENTS

| 3,368,940 | 2/1968 | Turner, Jr. et al. ............. 260/112 T |
| 3,654,083 | 4/1972 | Moelker ................................ 195/63 |
| 3,706,633 | 12/1972 | Katchalski et al. .................... 195/63 |
| 3,909,358 | 9/1975 | Stanley et al. ......................... 195/63 |
| 4,004,979 | 1/1977 | Avrameas et al. ..................... 195/68 |

OTHER PUBLICATIONS

Chemical Abstract 85, 118835j, (1976) of Japan, Kokai 76,482, Jul. 2, 1976.

*Primary Examiner*—Lionel M. Shapiro
*Attorney, Agent, or Firm*—M. Howard Silverstein; David G. McConnell; Theodore J. Leitereg

[57] ABSTRACT

Insolubilized but active enzymes are prepared by mixing an aqueous solution of the enzyme with an aqueous solution of chitosan and then adding a polyfunctional cross-linking agent to form a gel. The so-produced gel is reacted with a reducing agent to form a granular insolubilized enzyme, which has retained a substantial part of its original activity.

17 Claims, No Drawings

METHOD FOR INSOLUBILIZING ENZYMES ON CHITOSAN

BACKGROUND OF THE INVENTION

1. Field of the Invention

This invention relates to and has among its objects the provision of novel water-insoluble but active enzyme products and methods for preparing them. Further objects of the invention will be evident from the following description wherein parts and percentages are by weight unless otherwise specified.

2. Description of the Prior Art

In recent years there has been considerable interest in preparing enzymes in insolubilized (sometimes referred to as immobilized) form. Such products enable enzyme catalysed reactions to be carried out in a simplified and efficient manner. Typically, the insolubilized enzyme is placed in a cylindrical vessel and a solution of the substrate to be reacted is passed through the enzyme column. The reaction takes place within the column and the effluent liquor contains the reaction products. With this system the enzyme can be used repeatedly for processing fresh batches of the substrate. Various techniques have been advocated for preparing insolubilized enzymes. One procedure is to entrap the enzyme in polymerizing polyacrylamide; another is to adsorb it on insoluble media such as ion exchange resins, alumina, etc.

SUMMARY OF INVENTION

In accordance with the invention insolubilized enzymes are prepared from enzymes which are in a norml or native (soluble) state by mixing an aqueous solution of the enzyme with a slightly acidic aqueous solution of chitosan. A polyfunctional cross-linking agent is added to the mixture to form a gel, which is treated with a reducing agent to produce a granular material containing the active enzyme.

A primary advantage of the products of the invention is that their activity is retained over long periods of use. Thus, the products of the invention have the advantage not only of being reusable, but also usable under conditions of continuous operations for long periods of time and with large amounts of substrates.

Another advantage of the product of the invention is that it has a granular texture. Consequently, the instant product acts as its own carrier or support so that it can be formed into a column through which water and other liquids can percolate readily. This is in sharp contrast to known insolubilized enzymes which are generally amorphous materials that cannot be used directly in a column because liquids will not flow therethrough. These known products require the addition of a carrier such as diatomaceous earth, crushed firebrick, or the like to provide a liquid-permeable mass.

Another advantage of the invention is that the products are afforded by simple procedures using readily-available reactants. No exotic chemicals or complicated procedures are required. Nonetheless, the products retain a significant and sufficient part of the activity of the starting enzyme. In some cases the major part of the original activity is retained.

A further advantage of the invention is that useful products can be prepared from any enzyme source, including pure enzymes, enzyme concentrates, crude enzyme preparations, and even such substances as animal organs, plant parts, microbial cultures, and the like. Important in this regard is that application of the herein-described reactants causes most of the active enzyme to be selectively precipitated even where it is present in minute quantity, e.g., as little as 1 mg. of active enzyme in association with gram quantities of inactive components. Accordingly, the invention provides the means for preparing insolubilized products from enzymes which previously were difficult to insolubilize or which were never insolubilized.

Another advantage of the invention lies in the precise control that one can exercise over the extent and direction of enzymic reactions. This results because of the solid nature of the products of the invention which allows specific amounts to be metered out to suit any particular situation.

Another advantage of the invention is that external forces, such as heat, acid, and the like, which might be detrimental to the enzyme, need not be applied to stop the reaction. It is only necessary to separate the granular product from the solution in order to short-stop the reaction.

A further advantage of the invention is explained as follows: Most enzymes have an optimum pH, that is, a pH value at which the enzyme exhibits maximum activity. We have found that insolubilizing an enzyme in accordance with the invention produces a shift in this optimum pH, generally to a lower value. This particular aspect of the invention is quite important where an acidic food product (e.g., a fruit juice) is to be treated enzymatically, since it yields efficient results with enzymes which normally would operate inefficiently at the low pH provided by the acidic food.

DESCRIPTION OF THE PREFERRED EMBODIMENTS

The term "dispersion" used herein includes dispersions, solutions, emulsions, suspensions, mixtures, and the like.

In a first step in the process of the invention the enzyme to be insolubilized is dissolved in distilled water. Where necessary the pH of the water is adjusted by conventional methods such as adding an acid, buffer, etc., to a level at which the enzyme is soluble. Appropriate pH's to use with any particular enzyme are described in the literature. In many cases a pH of about 3 to 7 is employed. It may further be noted that oftentimes the starting material already contains a buffer or other pH-adjusting agent so that when it is mixed with water the resulting dispersion will exhibit a pH at which the enzyme is most soluble. This is particularly the case with commercially-available enzyme perparations. It is obvious that in such cases there is no need to apply any pH adjustment.

Following preparation of the aqueous solution of the starting material, a mechanical separation step such as filtration or decantation can be applied to remove fillers, debris, or other undissolved material.

Next, chitosan is dissolved in water. Generally, it is necessary to add a small amount of acid to the water in order to effect solution of the chitosan. The amount of acid is generally that necessary to adjust the pH of the dispersion to about from 3 to 7. Usually, this amount is about 4 to 5 milliequivalents of acid per gram of chitosan. As the acid, one may use hydrochloric acid, phosphoric acid, acetic acid, and the like. Furthermore, one may employ a buffer to attain the desired pH level and effect solubilization of the chitosan.

Chitosan is a polyamino polysaccharide obtained by N-deacetylation of chitin with strong alkali and heat. Chitin is a polysaccharide wherein the primary repeating unit in the molecule is 2-deoxy-2-(acetylamino) glucose. In general, about one out of every six units in chitin is not acetylated, whereas in chitosan essentially all the repeating units are not acetylated. It should be noted that the extent of non-acetylation can be controlled by the severity of the deacetylation reaction.

Chitin is readily prepared by removing the impurities from shells of crab, shrimp, lobsters, crayfish, and the like, which are abundantly available from seafood processing plants, and from exoskeletons of insects.

Next, the aqueous dispersion of starting enzyme is mixed with the aqueous dispersion of chitosan. Generally, about 10 to 100 milligrams of crude enzyme per gram of dry chitosan are used. The mixture is gently agitated by conventional means such as shaking, stirring, or the like while being held for approximately 5-20 minutes at a temperature of about from 10to 25C.

It should be noted that the enzyme and the chitosan can be simultaneously dissolved in water to produce the mixture directly.

To the above mixture is added a polyfunctional cross-linking agent i.e., one with more than one functional moiety, such as a di- or polyaldehyde, a di- or polyisocyanate, a di- or polyacid chloride, and the like. Usually, the polyfunctional cross-linking agent is dissolved in water and the resulting aqueous solution is added to the above mixture. The amount of polyfunctional cross-linking agent is not critical; 1 to 50 parts thereof per part of enzyme, may be used. The unreacted residue is removed in a subsequent washing step.

The resulting mixture is held for a period of time to ensure proper formation of a gel. Usually, the mixture is held for a short period, about 30 to 60 minutes, at ambient temperature. However, the holding can be conducted at temperatures between 10-25° C., the duration of the holding period decreasing as the temperature increases. The polyfunctional cross-linking agent must contain more than one functional group. For example, one may employ a polyaldehyde, i.e., a compound containing more than one aldehyde function, such as glyoxal, glutaraldehyde, dialdehyde starch (DAS), succinaldehyde, malonaldehyde, adipaldehyde, pimelaldehyde, and the like. As the polyisocyanate, one may employ cyclohexyl diisocyanate, 4,4' dicyclohexylmethane diisocyanate, hexamethylene diisocyanate, dimer oleic acid diisocyanate, 1-isocyanato-3,3,5-trimethyl-5-isocyanato-methylcyclohexane, N-(1,1-dimethyl-3-oxo-butyl) acrylamide and its hydroxy-methylated derivative, hexadecane diisocyanate, etc. Other polyfunctional cross-linking agents will be suggested to those in the art from an understanding of the description of the instant process.

The so-formed gel is mixed with a reducing agent of sufficient reductive capacity to produce a granular material from the gel. It should be obvious that the reducing agent must be selected for its ability to form the gel into a granular product without interfering with the activity of the enzyme. Reducing agents that satisfy this limitation are certain borohydride reducing agents such as sodium borohydride, sodium cyanoborohydride, and the like. Contact between the gel and the reducing agent should be maintained for about 1 to 60 minutes at a temperature of 4°-20° C. or until a suitable granular material has been formed. The concentration of reducing agent should be sufficient to produce a granular product from the gel; generally, the concentration of reducing agent is about from 2 to 10 parts per part of crude enzyme.

During the reduction reaction heat is generated. Consequently, the reaction mixture should be cooled to maintain the temperature between about 4° to 20° C.

It should be noted that the mixture of the aqueous solution of the enzyme and the aqueous solution of chitosan may be treated simultaneously with a polyfunctional cross-linking agent and a reducing agent. In this particular embodiment of the invention a gel forms and is immediately acted upon by the reducing agent to yield a granular product. This embodiment of the invention has the advantage of ease of operation.

The granular product is then collected by filtration and washed several times with distilled water to remove excess reagents. The so-prepared insolubilized enzyme is ready for use.

Usually, the starting enzyme contains inactive proteins and it is desirable to remove these from the final product. To this end the insolubilized enzyme is washed with distilled water for a long period, e.g., about 60 minutes. It is then soaked sequentially in (a) several volumes of 10-15% aqueous soduim chloride, (b) a potassium acetate buffer at pH 7, and, finally, (c) a potassium acetate buffer at a pH whereat the enzyme product exhibits maximum activity. The so-prepared and purified product is collected by filtration and is ready for use.

The invention is of wide versatility and can be applied to enzymes of all kinds, illustrative examples being alcohol dehyrogenase, amino acid oxidase, $\alpha$- and $\beta$-amylases, arginase, asparaginase, catalase, cellulase, chymotrypsin, collagenase, deoxyribonuclease, diaphorase, elastin, emulsin, ficin, glucose oxidase, histidase, hyaluronidase, invertase, lactase, peroxidase, phosphatases, lipase, lipoxidase, lysozyme, papain, chymopapain, pepsin, pectin methyl esterase, polyphenol oxidase, rennin, ribonuclease, trypsin, tyrosinase, urease, etc. The starting enzyme need not be a purified substance but may be a preparation containing an enzyme. Thus, for example, one may employ microbial preparations which contain enzymes, typically, cultures or cells of yeasts, molds, bacteria, and the like. Other enzyme-containing preparations which may be applied to the process of the invention are such materials as animal organs, e.g., pancreas, liver, etc., insects and insect parts, barley malt, pineapple, papaya, etc.

The products of the invention can be utilized in a variety of ways. A few examples are provided below by way of illustration and not limitation. Whey, currently a waste material in the production of cheese, can be converted efficiently to glucose and galactose, which are useful as fermentation media and the like, by contacting the watery whey with an insolubilized lactase product prepared in accordance with the invention. An insolubilized protease enzyme can be employed to prevent turbidity in beer, wine, fruit juices, etc. Other applications include hydrolyzing starch to glucose, inverting sucrose solutions for the manufacture of candy, conversion of glucose to fructose, de-glucosing egg whites, conversion of dilute alcohol solutions to vinegar, etc.

It is believed that formation of the products of the invention involves the following mechanism: The polyfunctional agent promotes cross-linking of the solubilized chitosan in the presence of an enzyme. The lysyl residues of the enzyme might participate in the cross-linking reaction and thereby become covalently fixed to the chitosan polymer. The cross-linked material has the texture of a gel and is a type of Schiff-base polymer. When the gel is treated with a reducing agent the Schiff-base polymer matrix is reduced and stabilized, thus yielding a granular product.

Another possibility is that the enzyme may be fixed to the polymer matrix by entrapment or interfacial deposition. However, regardless of the mechanism, the enzymes do become insolubilized and are not removed from the product during use. Thus, it is not meant to limit the invention to a particular mechanism involved in the formation of the product.

EXAMPLES

The invention is further demonstrated by the following illustrative examples.

EXAMPLE 1

Preparation of Insolubilized Lactase

Run 1: A solution of 7 g. of dry chitosan in 250 ml. of water containing 30 ml. of 1 N HCL acid to effect solution. To this solution was added a solution of 0.5 g. of commercial grade lactase (a $\beta$-galactosidase) in 50 ml. of water. The crude enzyme hydrolyzed about 10 micromoles of lactose per mg. per minute at pH 4 and 40° C. The mixture was swirled for 5 minutes and added to 100 ml. of aqueous solution containing 7 g. of dialdehyde starch (DAS) that had been solubilized with 2.5 millimoles of sodium carbonate. The solubilized DAS solution had a pH of about 7. The resulting mixture was held for a period of 30 minutes until a gel formed. Then, the mixture was cooled to and maintained at about 10° C. and stirred mechanically, and 2 g. of pelletized sodium borohydride (about 0.3 each pellet) was added, over a period of about 15 minutes. Stirring was continued for another 15 minutes. The insolubilized product took on a granular form, shortly after the start of addition of borohydride.

The granular product was separated from the reaction mixture by filtration and washed with distilled water, followed by 0.5 M phosphate buffer (potassium dihydrogen phosphate and disodium hydrogen phosphate mixture) of pH 7.0, then with phosphate buffer of pH 5.6, and finally with distilled water.

Run 2: The procedure outlined above for Run 1 was followed with the following changes: (a) One (1) g. of lactase was employed; (b) 30 ml. of a 30% aqueous solution of glyoxal (pH 7) was used instead of the DAS solution; and (c) 5 g. of sodium borohydride was employed as the reducing agent.

Run 3: The procedure outlined in Run 1 was employed except that (a) 2.4 g. of chitosan was dissolved in 5 ml. of 2 M acetic acid, 115 ml. of water, and 5 ml. of 1 M sodium acetate buffer of pH 5.4; the final pH of the solution was 5.4; (b) 120 mg. of crude lactase was used; (c) 375 mg. of glutaraldehyde in 150 ml. of water was used; and (d) 100 mg. of sodium borohydride in 50 ml. of water was used as the reducing agent.

The lactase activity of the products was measured in a shaker bath batch test at 40° C. with 25 ml. of 0.4 M lactose solution in a 0.1 M potassium acetate buffer, pH 4.0; 0.5 g. of moist product was employed. The production of glucose (micromoles per minute per g. of moist product) was measured. The results are tabulated below.

| Run | Insolubilized enzyme | | Activity Micromoles of glucose produced per min. per gram of moist insolubilized enzyme product* |
|---|---|---|---|
| | Enzyme | Cross-linker | |
| 1 | lactase | DAS | 21.3 |
| 2 | lactase | glyoxal | 43.0 |
| 3 | lactase | glutaraldehyde | 31.0 |

*The insolubilized enzyme products contained 85-90% water.

EXAMPLE 2

Preparation Insolubilized Invertase

The procedure outlined in Example 1, Run 3, was followed except that yeast invertase was used in place of lactase. The insolubilized product contained about 86% water.

The invertase activity of the product was measured in a shaker bath batch test at 40° C. with 100 ml. of 0.1 M sucrose solution in 0.1 M phosphate buffer at pH 5.0; using 1.0 g. of moist product. The rate of hydrolysis of sucrose was determined by measuring the micromoles of glucose formed per minute per gram of moist product and was found to be 48.

Having thus described our invention, we claim:

1. A process for preparing an insoluble but active enzyme, which comprises
   (a) dissolving a soluble active enzyme in water,
   (b) dissolving chitosan in water,
   (c) mixing the aqueous solution of the enzyme with the aqueous solution of chitosan,
   (d) adding polyfunctional cross-linking agent to the mixture to produce a gel containing the enzyme, and
   (e) adding a reducing agent to the so-formed gel, said reducing agent being of sufficient reductive ability to produce a granular material from the gel but insufficient to lower the activity of the enzyme.

2. The process of claim 1 wherein the chitosan is dissolved in water at pH 7–7.

3. The process of claim 1 wherein the enzyme and chitosan are simultaneously dissolved in water.

4. The process of claim 1 wherein the polyfunctional cross-linking agent and the reducing agent are simultaneously added to the aqueous mixture of the enzyme and chitosan.

5. The process of claim 1 wherein the polyfunctional cross-linking agent is an aldehyde containing more than one aldehyde function.

6. The process of claim 1 wherein the polyfunctional cross-linking agent is an isocyanate containing more than one isocyanate function.

7. The process of claim 1 wherein the reducing agent is sodium borohydride.

8. The process of claim 1 wherein the reducing agent is sodium cyanoborohydride.

9. The process of claim 1 wherein the enzyme is a sugar-hydrolyzing enzyme.

10. The process of claim 1 wherein the enzyme is invertase.

11. The process of claim 1 wherein the enzyme is a glucose-oxidizing enzyme.

12. An insoluble but active enzyme comprising a soluble enzyme and chitosan cross-linked with a polyfunctional agent into a gel and then granularized with a reducing agent.

13. The product of claim 12 wherein the enzyme is a sugar-hydrolyzing enzyme.

14. The product of claim 12 wherein the enzyme is invertase.

15. The product of claim 12 wherein the enzyme is a glucose-oxidizing enzyme.

16. The product of claim 12 wherein the polyfunctional cross-linking agent is an aldehyde containing more than one aldehyde function.

17. The product of claim 12 wherein the polyfunctional cross-linking agent is an isocyanate containing more than one isocyanate function.